(12) United States Patent
Quant et al.

(10) Patent No.: US 9,506,869 B2
(45) Date of Patent: Nov. 29, 2016

(54) HANDHELD LASER INDUCED BREAKDOWN SPECTROSCOPY DEVICE

(71) Applicant: TSI, Incorporated, St. Paul, MN (US)

(72) Inventors: Frederick Quant, Shoreview, MN (US); Kenneth R. Farmer, Lake Elmo, MN (US); Phillip V. Tan, Shoreview, MN (US); Christopher B. Stipe, Bothell, WA (US); Steven G. Buckley, Redmond, WA (US); Erik Stockinger, Seattle, WA (US); Daniel Jensen, Vadnais Heights, MN (US)

(73) Assignee: TSI, Incorporated, St. Paul, MN (US)

( * ) Notice: Subject to any disclaimer, the term of this patent is extended or adjusted under 35 U.S.C. 154(b) by 0 days.

(21) Appl. No.: 14/514,294

(22) Filed: Oct. 14, 2014

(65) Prior Publication Data
US 2015/0103334 A1 Apr. 16, 2015

Related U.S. Application Data

(60) Provisional application No. 61/891,743, filed on Oct. 16, 2013.

(51) Int. Cl.
*G01N 21/71* (2006.01)
*G01J 3/443* (2006.01)
(Continued)

(52) U.S. Cl.
CPC ........... *G01N 21/718* (2013.01); *G01J 3/0221* (2013.01); *G01J 3/0272* (2013.01);
(Continued)

(58) Field of Classification Search
CPC ........ G01J 3/0272; G01J 3/02; G01J 3/0291; G01J 3/0264; G01J 3/50; G01J 3/0218; G01J 3/10; G01J 3/0278; G01J 2003/2866; G01J 3/502; G01J 3/18; G01J 1/0271; G01J 1/0233; G01J 3/0248; G01J 5/0265; G01J 5/04; G01J 5/0818; G01J 1/42; G01N 2201/0221; G01N 21/474; G01N 21/255; G01N 21/29; G01N 2201/0612; G01N 21/718; G01N 21/23
USPC .............................. 356/51, 326, 328, 402, 73
See application file for complete search history.

(56) References Cited

U.S. PATENT DOCUMENTS

| 4,550,381 A | 10/1985 | Waechter et al. |
|---|---|---|
| 4,631,452 A | 12/1986 | Harry |

(Continued)

FOREIGN PATENT DOCUMENTS

| AU | 747362 | 5/2002 |
|---|---|---|
| EP | 1 936 361 | 6/2008 |

(Continued)

OTHER PUBLICATIONS

Host-dependence of Trivalent Erbium (Er3+) Spectra Relevant to Solid-state Lasers: Yttrium Aluminum Garnet (YAG) and Sesquioxides by Merkle et al., Army Research Lab report (ARL-TR-5755; Sep. 2011).*

(Continued)

*Primary Examiner* — Tarifur Chowdhury
*Assistant Examiner* — Mohamed K Amara
(74) *Attorney, Agent, or Firm* — Kagan Binder, PLLC

(57) ABSTRACT

A novel device, method and systems disclosed managing the thermal challenges of LIBS laser components and a spectrometer in a handheld structure as well the use of simplified light signal collection which includes a bare fiber optic to collect the emitted light in close proximity to (or in contact with) the test material. In one example embodiment of the handheld LIBS device, a burst pulse frequency is 4 kHz is used resulting in a time between pulses of about 250 μs which is a factor of 10 above that of other devices in the prior art. In a related embodiment, an active Q-switched laser module is used along with a compact spectrometer module using a transmission grating to improve LIBS measurement while substantially reducing the size of the handheld analyzer.

10 Claims, 9 Drawing Sheets

(51) Int. Cl.
*G01J 3/02* (2006.01)
*G01J 3/18* (2006.01)
(52) U.S. Cl.
CPC ............. *G01J 3/0291* (2013.01); *G01J 3/18* (2013.01); *G01J 3/443* (2013.01); *G01J 2003/1861* (2013.01); *G01N 2201/0221* (2013.01); *G01N 2201/0697* (2013.01)

(56) References Cited

U.S. PATENT DOCUMENTS

| | | |
|---|---|---|
| 5,070,300 A | 12/1991 | Matsui et al. |
| 5,847,825 A | 12/1998 | Alexander |
| 6,034,768 A | 3/2000 | Fraser et al. |
| 6,762,836 B2 | 7/2004 | Benicewicz et al. |
| 6,771,368 B1 | 8/2004 | Chadwick |
| 6,801,595 B2 | 10/2004 | Grodzins et al. |
| 6,836,325 B2 | 12/2004 | Maczura et al. |
| 6,862,092 B1 | 3/2005 | Ibsen et al. |
| 6,922,423 B2 | 7/2005 | Thornton |
| 6,922,578 B2 | 7/2005 | Eppstein et al. |
| 7,016,035 B2 | 3/2006 | Wu et al. |
| 7,039,075 B2 | 5/2006 | Thornton |
| 7,092,083 B2 | 8/2006 | Chadwick et al. |
| 7,092,087 B2 | 8/2006 | Kumar et al. |
| 7,164,121 B2 | 1/2007 | Hirano et al. |
| 7,233,643 B2 | 6/2007 | Sipila et al. |
| 7,236,243 B2 | 6/2007 | Beecroft et al. |
| 7,283,242 B2 | 10/2007 | Thornton |
| 7,298,475 B2 | 11/2007 | Gandhi et al. |
| 7,394,537 B1 | 7/2008 | Lindfors et al. |
| 7,426,019 B2 | 9/2008 | Eklin |
| 7,515,262 B2 | 4/2009 | Sirat et al. |
| 7,542,138 B2 | 6/2009 | Gardner, Jr. |
| 7,557,917 B1* | 7/2009 | Beesley ................. 356/318 |
| 7,821,634 B2 | 10/2010 | Dillon et al. |
| 7,838,825 B2 | 11/2010 | Vakhshoori et al. |
| 7,839,904 B1* | 11/2010 | Equall et al. ............... 372/10 |
| 7,936,455 B2 | 5/2011 | Beardsley et al. |
| 7,999,928 B2 | 8/2011 | Beckstead et al. |
| 8,125,627 B2 | 2/2012 | Dottery et al. |
| 8,436,991 B2 | 5/2013 | Senac |
| 8,619,255 B2 | 12/2013 | Gennadievich |
| 8,687,177 B2 | 4/2014 | Beckstead et al. |
| 2002/0093653 A1* | 7/2002 | Detalle et al. ............. 356/318 |
| 2003/0147072 A1 | 8/2003 | Whitehouse |
| 2003/0174325 A1* | 9/2003 | Zhang et al. .............. 356/318 |
| 2004/0051867 A1* | 3/2004 | Brestel ............... G01J 3/2889 356/318 |
| 2005/0167405 A1 | 8/2005 | Stoltz et al. |
| 2006/0084957 A1 | 4/2006 | Delfyett et al. |
| 2007/0057188 A1* | 3/2007 | Chou ................. G01J 3/443 250/341.1 |
| 2008/0105664 A1 | 5/2008 | Smart |
| 2008/0149838 A1* | 6/2008 | Parvin ..................... 250/356.2 |
| 2008/0151241 A1 | 6/2008 | Lindfors et al. |
| 2010/0047916 A1* | 2/2010 | Rothschild ............ G01J 3/10 436/98 |
| 2011/0100967 A1* | 5/2011 | Yoo et al. .................. 219/121.73 |
| 2011/0290026 A1* | 12/2011 | Rice et al. ........................ 73/602 |
| 2011/0306865 A1* | 12/2011 | Thornton et al. ............. 600/407 |
| 2012/0033212 A1 | 2/2012 | Barefield, II |
| 2012/0084016 A1 | 4/2012 | Davis |
| 2012/0206722 A1* | 8/2012 | Grigoropoulos et al. .... 356/318 |
| 2012/0249781 A1* | 10/2012 | Vollmerhausen ............. 348/135 |
| 2013/0169961 A1* | 7/2013 | Kraft ............................ 356/318 |
| 2013/0277340 A1* | 10/2013 | Liu et al. .................. 219/121.61 |
| 2014/0022531 A1 | 1/2014 | Sackett |
| 2014/0022532 A1 | 1/2014 | Sackett |
| 2014/0176940 A1* | 6/2014 | Fishbine et al. ............. 356/301 |
| 2014/0202490 A1 | 7/2014 | Day |
| 2014/0204375 A1 | 7/2014 | Day |
| 2014/0204376 A1 | 7/2014 | Day |
| 2014/0204377 A1 | 7/2014 | Day |
| 2014/0204378 A1 | 7/2014 | Day |

FOREIGN PATENT DOCUMENTS

| | | | |
|---|---|---|---|
| WO | 00/14516 | 3/2000 | |
| WO | WO 03006967 A1 * | 1/2003 | ............ G01N 21/71 |
| WO | 03/021238 | 3/2003 | |
| WO | WO 2014/113824 | 7/2014 | |

OTHER PUBLICATIONS http://assets.newport.com/webDocuments-EN/images/20063.PDF.*
Pierce et al., "Field-testing for environmental pollutants using briefcase sized portable LIBS system" LIBS 2004, 3$^{rd}$ International Conference on Laser Induced Plasma Spectroscopy and Applications, pp. 1-14, 2004.
G. Galbacs, et al. "A Study of Ablation, Spatial, and Temporal Characteristics of Laser-Induced Plasmas Generated by Multiple Collinear Pulses" Applied Spectroscopy, vol. 64, No. 2, pp. 161-172, 2010.
DeLucia, Jr., et al. "Laser-Induced Breakdown Spectroscopy (LIBS): A Promising Versatile Chemical Sensor Technology for Hazardous Material Detection," IEEE Sensors Journal, vol. 5, No. 4, Aug. 2005, pp. 681-689, (9 pages).
Harmon et al., "Man-Portable LIBS for Landmine Detection," Proc. of SPIE vol. 6217 62170I-1, 2006 (7 pages).
Ibsen photonics, Freedom VIS 360-830 nm OEM Spectrometer, Published Oct. 13, 2014.
Ibsen photonics, Freedom UV 190-435 nm OEM Spectrometer, Published Oct. 13, 2014.
Kigre, Inc., MK-367 Laser System Version 3.2, Oct. 21, 2011.
Myers, et al., "LIBS system with compact fiber spectrometer, head mounted spectra display and hand held eye-safe erbium glass laser gun," SPIE Photonics West 2010, Solid State Laser XIX: Technology and Devices Conference LA101, # 7578-87, Jan. 26, 2010, (20 pages).
Rasmussen, "Overview of High-Efficiency Transmission Gratings for Molecular Spectroscopy," Spectroscopy 29(4), Apr. 2014, pp. 32-39 (6 pages).
Wu et al., "1.2J High Energy Diode Pumped 1535 mn Er3+, Yb3+: Glass Laser," Kigre Inc., Presented at CLEO/Europe—EQEC'96, Congress Centrum Hamburg Germany, 1996, (12 pages).
International Search Report and Written Opinion, PCT/US2014/060611, mailed Apr. 9, 2015.

* cited by examiner

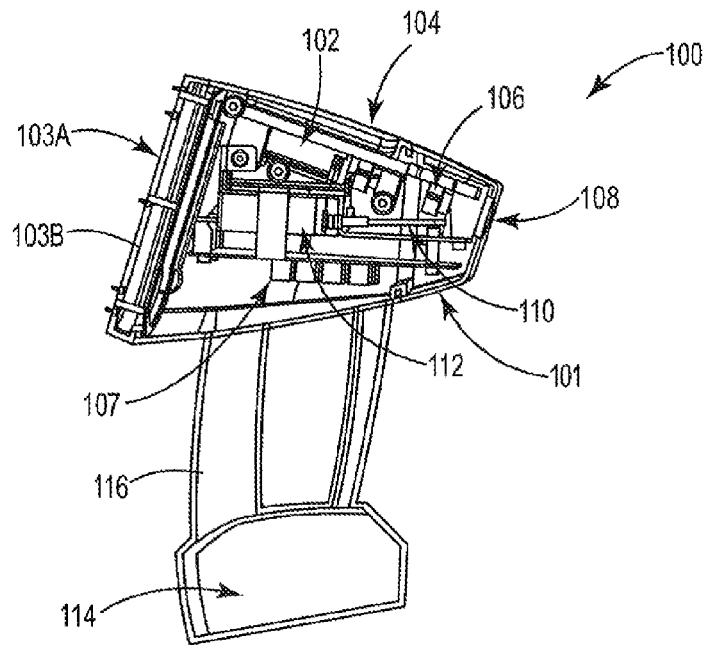
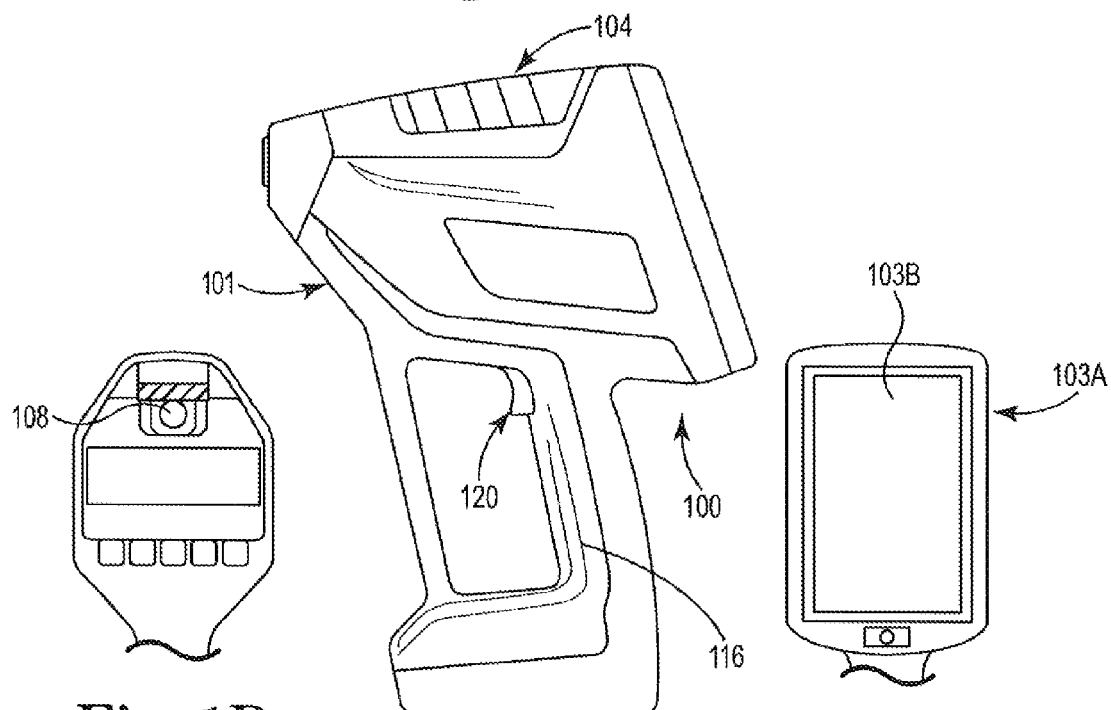

PRECISION: SP VS. PT
SAMPLE 7075

| ELEMENT | SINGLE PULSE MODEL RSD (%) | | | | PULSE TRAIN MODE RSD (%) | |
|---|---|---|---|---|---|---|
| | SINGLE SHOT | 10-SHOTS | 25-SHOTS | 150-SHOTS | SINGLE SHOT (10) | 15-SHOTS (150) |
| Mg (2.57%) | 15.4 | 7.8 | 5.6 | 5.3 | 13.5 | 3.6 |
| Cu (1.57%) | 12.9 | 6.9 | 8.5 | 9/7 | 13.5 | 6.3 |
| Al | 13.9 | 5.4 | 5.7 | 3.2 | 14.8 | 3.2 |

Fig. 3

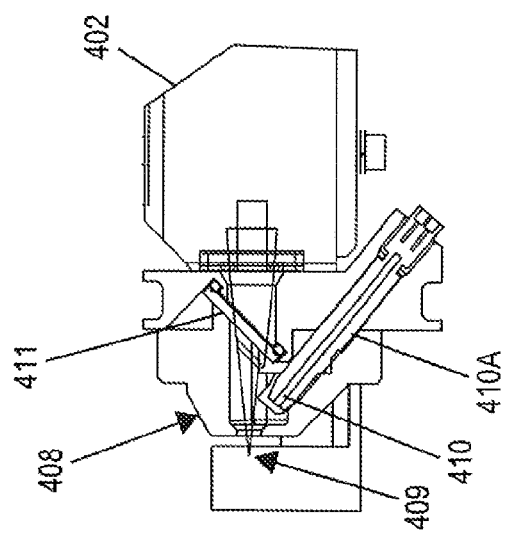
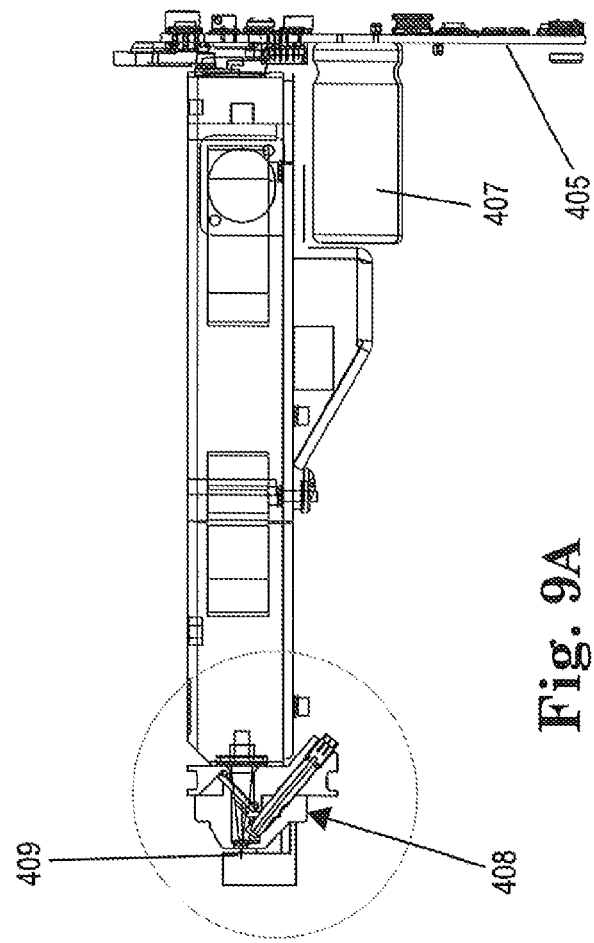

HANDHELD LASER INDUCED BREAKDOWN SPECTROSCOPY DEVICE

CLAIM OF PRIORITY

This application claims priority to and the benefit of U.S. Provisional Patent Application No. 61/891,743, filed Oct. 16, 2013 and titled "HANDHELD LASER INDUCED BREAKDOWN SPECTROSCOPY DEVICE" which application is incorporated herein by reference in its entirety.

FIELD AND BACKGROUND

The invention is generally in the field of laser-induced breakdown spectroscopy (LIBS) and more particularly an apparatus and system designed for laser-induced breakdown spectroscopy measurements.

For various applications, methods are needed for determining the material constitution of a sample. One of the known methods is laser-induced breakdown spectroscopy (LIBS), which involves focusing a laser beam onto a surface of a sample with a high enough power density to transform a small part of the sample material into a state of plasma. Optical emissions from the plasma plume are collected with light collection configuration, and the spectral distribution (i.e. intensity as a function of wavelength) of the collected optical emissions is analyzed in a spectrometer that produces information in electronic form describing the spectral distribution. Since atomic and molecular constituents of sample materials have characteristic optical emission spectra, the information produced by the spectrometer reveals the constituents of that part of the sample onto which the laser beam was focused or directed.

The sample may in principle be solid, liquid or gaseous. In the case of a gaseous sample the concept of a "surface" of the sample does not exist, but the laser beam is just focused into the gaseous sample. A drawback of the known LIBS measurement devices is its certain bulky structure and limited applicability to field use. Traditionally LIBS has been considered to be applicable under laboratory conditions only. Efforts have been made to reduce the form factor of LIBS devices, as evidenced by U.S. Pat. No. 7,394,537 to Lindfors et al and U.S. Pat. No. 7,821,634 to Dillon et al. However, these devices still create safety issues for the users and the laser components are still subject to damage when in portable form due to the requisite size for energy consumption and stabilization of the output wavelength, among other limitations including heat consumption, complex optics for light collection and lack of a robust design for continuous alloy analysis.

SUMMARY

There is provided herein a handheld LIBS device that is eye-safe for the user and that can collect spectral measurements quickly and with a reasonably high degree of accuracy for the intended industrial and commercial application. Other advantages include taking measurements with a built-in spectrometer more quickly than in prior art LIBS devices, while emitting about ⅓ of the heat as other devices, thereby prolonging the life of the laser source and reducing battery consumption. A newly configured handheld LIBS device also facilitates the use of a bare fiber optic component that will collect light and signal samples at close proximities to the material to be tested thereby substantially simplifying the optics arrangement necessary to collect the light signals generated by the impinged laser light on the test material.

In one example embodiment of our invention, there is provided a handheld LIBS device configured for use to primarily differentiate and identify aluminum alloys. Such device is small, lightweight, powered by a battery, and is environmentally protected for outdoor use. The handheld LIBS device of this example embodiment is able to characterize an aluminum sample in terms of elemental concentrations and other metal alloys are expected to be identified and elemental concentrations determined, with a primary advantage of the LIBS over XRF being its ability to determine the elemental concentration of light elements such as Li, B, Be, C, Al, Na and Mg. An advantage to this example embodiment is that it can perform rapid analyses with little to no surface preparation while using a laser source that operates with sufficient energy to burn through contamination, but optically designed to be eye-safe (an eye-safe wavelength, low laser energy per pulse, and a highly divergent laser beam design). In one example embodiment, the handheld measurement device uses a 1535 nanometer (nm) Er:glass laser (in a related embodiment an Er3:Yb3 laser can be configured by one skilled in the art to arrive at a similar eye-safe wavelength), rather than the standard 1064 nm laser, which is considered to be an "eye-safe" wavelength when coupled with appropriate beam focus and beam fluence modifications so the user will not be required to wear eye protection when using the handheld device.

Among the advantages of the aforementioned example handheld device is that it is configured to stably and repeatedly use a 1535 nm laser. This is unlike prior art devices as these 1535 nm lasers are known to have sensitivity to thermal shock and are not able to run at high repetition rates. Prior art devices also have very low pulse energies (e.g. uJ/pulse) and need to be used close to the sample material to be tested. In one example embodiment, the handheld LIBS device is configured to run the laser source and monitor the laser temperature so as to avoid laser damage and maintain consistent results. The laser temperature is monitored directly (using a thermocouple) and indirectly by measuring the amount of time for each laser current pulse (pulse width). Most prior art handheld devices use a single pulse (SP) of laser energy to generate the plasma plume from the sample to be tested. Conversely, the teachings herein provide a handheld LIBS device that utilizes instead a novel "burst mode" in which a pulse train (PT) of small pulses in combination with a spectrometer configured to capture all of the signals and integrate them into a single data point to effectively and substantially boost the signal over what would be obtained if the same laser energy was delivered in a single pulse. These innovations allow the eye-safe 1535 nm laser to be effectively used for performing LIBS measurements in a small form factor and with a high duty cycle that was previously unobtainable. This specific laser and its method of operation are new to the commercial LIBS market.

Nd:YAG lasers are typically used for LIBS devices because of their low cost. However, using a 1535 nm laser for this purpose, especially in a handheld device, was previously not commercially viable since most 1535 nm lasers are sensitive to thermal shock and typically cannot operate properly at repetition rates greater than 1 Hz. Further, single shots from the laser source on the test material only produce a relatively small signal and the optics required to capture such a signal make it expensive and cumbersome. The user requires a faster response for such a handheld device to be acceptable to the market. Hence, running the system in a burst mode whereby several pulses are generated from one pumped pulse facilitated by effective thermal management facilitates the reduction in size and increases the stability of the 1535 nm laser handheld device. This unique "burst mode" feature greatly cuts down analysis time and substantially improves the return signal compared with using a single pulse approach. One of the challenges that was overcome in developing this product was to characterize the behavior of the laser in this burst mode, which involved a unique implementation of a thermal management system including having a heat sink for the laser placed on the exterior of the instrument to cool the laser, while at the same time using the heat sink as an sighting piece for easily locating the sample-to-laser position.

In this example embodiment, the handheld LIBS device is configured to be safer for the user in comparison to XRF devices or even 1064 nm LIBS devices. The 1535 nm wavelength, combined with the low laser fluence (J/cm^2) beyond the ablation zone, ensures that the laser can be classified as Class I device, which is outside the range that can damage the human eye. Administrators and safety officers who approve and oversee products for use in workplaces have no restrictions for eye-safe, Class I laser products, whereas current Class IIIB handheld LIBS instruments in the marketplace today could require the use of safety glasses and/or controlled testing environments. In addition, using an eye-safe laser will benefit users and administrators as they will avoid the necessity to have radiation safety training and licensing, which is required with competitive XRF (X-ray fluorescence) technology. As an additional safety feature, the device is equipped with a proximity sensor to sense material in the target area before firing. The laser is by design, focused only at the sample location and diverges greatly beyond the sample plane.

The novel device, method and systems disclosed herein teach managing the thermal challenges of LIBS laser components and a spectrometer in a handheld structure as well the use of simplified light signal collection which includes a bare fiber optic to collect the emitted light in close proximity to (or in contact with) the test material. In one example embodiment of the handheld LIBS device, a burst pulse frequency is 4 kHz is used resulting in a time between pulses of about 250 μs which is a factor of 10 above that of other devices in the prior art. At 250 μs between pulses there would be little to no interaction between the pulses that would result in a change in the generated plasma plume. Without an enhanced plume, the handheld device can be held in close proximity to the test sample. In addition, the heat from the pulse train mode operation of the laser is monitored, dissipated and controlled in order to provide for such a compact and accurate design.

In one example embodiment, an apparatus for performing laser-induced breakdown spectroscopy is provided that includes a housing configured as a handheld apparatus and a diode-pumped laser module with a controller system operatively coupled thereto, the laser module including a solid laser medium and a passive Q-switched unit controlled by the controller so as to operate in a multiple pulse laser beam configuration. The apparatus also includes a fiber optic member configured to transfer light at a distal end of the fiber member from a plasma induced of a sample material by the multiple pulse laser beam and a spectrometer module configured to receive light from said fiber optic member and configured to produce a spectral distribution corresponding to the sample material from the multiple pulses. The apparatus includes a power source disposed within said housing and configured to deliver electric power to at least said pumped laser and said spectrometer, wherein the multiple pulse laser beam configuration includes multiple bursts of laser pulses with each burst separated from a subsequent burst by a first time to allow laser cooling, and wherein each pulse within each burst is separated by a second time to limit plasma continuation. In this embodiment, the multiple pulse laser beam configuration is in burst mode, the burst mode comprised of about 10-12 pulses at about 4 kHz, with each burst cycling at a frequency range of about 4 Hz to about 10 Hz. The apparatus further includes a heat sink member disposed on the housing near the distal end of the fiber member, wherein the heat sink member is adapted to be a sighting member for a distal end of the handheld apparatus. The apparatus also includes a spectrometer module that includes a first spectrometer configured to operate in an ultraviolet wavelength range and a second spectrometer configured to operate in a visible wavelength range.

In another example embodiment, method is provided of conducting laser induced breakdown spectroscopy measurements using an eye-safe laser source comprising the steps of generating a multiple pulse laser beam and directing the pulse laser beam to a sample material, wherein the multiple pulse laser beam includes multiple bursts of laser pulses with each burst separated from a subsequent burst by a first time to allow laser source cooling, and wherein each pulse within each burst is separated by a second time to limit plasma continuation. The next step is transferring light at a distal end of a fiber member from a plasma induced of the sample material by the multiple pulse laser beam and producing a spectral distribution from transferred light corresponding to the sample material from the multiple pulses. The method further comprises the step of sensing the sample material in the proximity of the distal end of the fiber before the step of generating the multiple pulse laser beam.

In a related example embodiment, an apparatus is provided for performing laser-induced breakdown spectroscopy that includes a housing configured as a handheld apparatus having an exit for electromagnetic radiation generated from within the housing and an active Q-switched Nd:YAG OPO (optical parametric oscillator) laser module with a controller system operatively coupled thereto disposed within the housing, the laser module configured to direct laser beam through the exit. The apparatus also includes a fiber optic member configured to transfer light at a distal end of the fiber member from a plasma induced of a sample material by the laser beam, the fiber optic member distal end disposed adjacent the exit and a spectrometer module configured to receive light from a proximal end of said fiber optic member and configured to produce a spectral distribution corresponding to the sample material from the received light. The apparatus also includes a sampling point interface member with a proximal opening disposed over the housing exit, the laser beam adapted to be projected through the proximal opening and through a distal opening of the interface member, the fiber optic member being disposed adjacent the interface member distal opening. In a related embodiment, the spectrometer module includes a first spectrometer configured to operate in an ultraviolet wavelength range and a second spectrometer configured to operate in a visible wavelength range. In another related embodiment, the apparatus further includes a power source disposed within the housing and configured to deliver electric power to at least the laser module and the spectrometer module and a display configured to display information and to receive commands from a user. The apparatus also includes a sighting member configured to assist a user in directing the laser beam, wherein the sighting member is selected from the group consisting of a heat sink member disposed above the laser module and a targeting LED member adapted to project light at a target on the sampled material. In a related embodiment, the apparatus includes at least one proximity sensor near the housing exit, the proximity sensor configured to sense location of sampled material. The apparatus in another embodiment includes a haptic feedback module configured to provide feedback that a sample analysis is at an acceptable precision level. The apparatus, in a related embodiment, includes a laser module that is configurable to emit laser beams at more than one energy level, a first energy level for cleaning of the sample material and a second energy level for analytical acquisition.

In accordance with one embodiment of the invention, a laser module includes a substrate, a reflective mirror, disposed on the substrate, adapted to reflect light of a first wavelength, and a gain block, disposed on the substrate, adapted to generate the light at the first wavelength and receive the light reflected from the reflective mirror; a Q switch, disposed on the substrate, adapted to receive and polarize the light from the gain block and provide pulsed light that is polarized and at the first wavelength. The laser module also includes a dichroic mirror, disposed on the substrate, adapted to pass the pulsed light from the Q switch and reflect light at a second wavelength; and an optical parametric oscillator crystal, disposed on the substrate, adapted to receive the pulsed light from the dichroic mirror and convert at least a portion of the pulsed light at the first wavelength into light at the second wavelength. The module also includes an output coupler mirror, disposed on the substrate, adapted to reflect light at the first wavelength and pass at least a portion of the light at the second wavelength to provide a laser output signal, wherein the reflective mirror and the output coupler mirror form a first resonant cavity, and the dichroic mirror and the output coupler mirror form a second resonant cavity within the first resonant cavity.

In yet another related embodiment, an apparatus is provided for interfacing a handheld laser induced breakdown spectroscopy apparatus with a sample material, the apparatus including an electromagnetic radiation source and an electromagnetic radiation detection and processing module. The apparatus also includes a housing configured to have an exit for the electromagnetic radiation and for capture of an emitted electromagnetic radiation from the sample material and includes a housing-to-sample material interaction section disposed about the housing exit, the interaction section having an area of less than 2 cm^2. In one example embodiment, the housing-to-sample interaction section is disposed at an end of a cone member, wherein the cone member has an opening greater than two times a diameter of the electromagnetic radiation. In a related embodiment, the housing-to-sample interaction section is disposed at an end of a cylinder member. In yet another related embodiment, a portion of the housing protrudes at a downward angle towards the housing exit, thereby enhancing the view of the interaction section and the sample material. In an example embodiment, the electromagnetic radiation source is an Nd:YAG OPO laser configured to project a laser beam through the housing exit and onto the sample material. In another example embodiment, the apparatus further includes a pierced mirror disposed within the housing and adjacent to the housing exit, wherein emitted light from the sample material is captured by the pierced mirror and transmitted to the electromagnetic radiation detection and processing module, wherein the electromagnetic radiation detection and processing module comprises a spectrometer module with at least one transmission grating. The apparatus, in a related embodiment, has an electromagnetic radiation source that is an X-ray device configured to project an X-ray beam through the housing exit and onto the sample material. The apparatus, in another embodiment, further includes a sampling point interface member with a proximal opening disposed over the housing exit, the electromagnetic radiation adapted to be projected through the proximal opening and through a distal opening of the interface member, an emitted signal transfer member being disposed adjacent the interface member distal opening, wherein the sampling point interface member eliminates autofocusing and increases electromagnetic radiation transfer by the emitted signal transfer member.

The novel features of the various embodiments the invention itself, both as to its construction and its method of operation, together with additional advantages thereof, will be best understood from the following description of specific embodiments when read in connection with the accompanying drawings.

BRIEF DESCRIPTION OF THE DRAWINGS

FIGS. 1A-1D illustrate various views of a handheld LIBS measurement apparatus according to an embodiment of the invention.

FIG. 3 there is illustrated a table comparing the measurements from a single pulse mode and a pulse train mode for a particular material sample having known quantities and percentages of Mg, Cu and Al.

FIGS. 9A-9B illustrate side and enlarged views of a sampling cone interface according to the teachings of the invention.

DETAILED DESCRIPTION OF THE INVENTION

Figure 2:
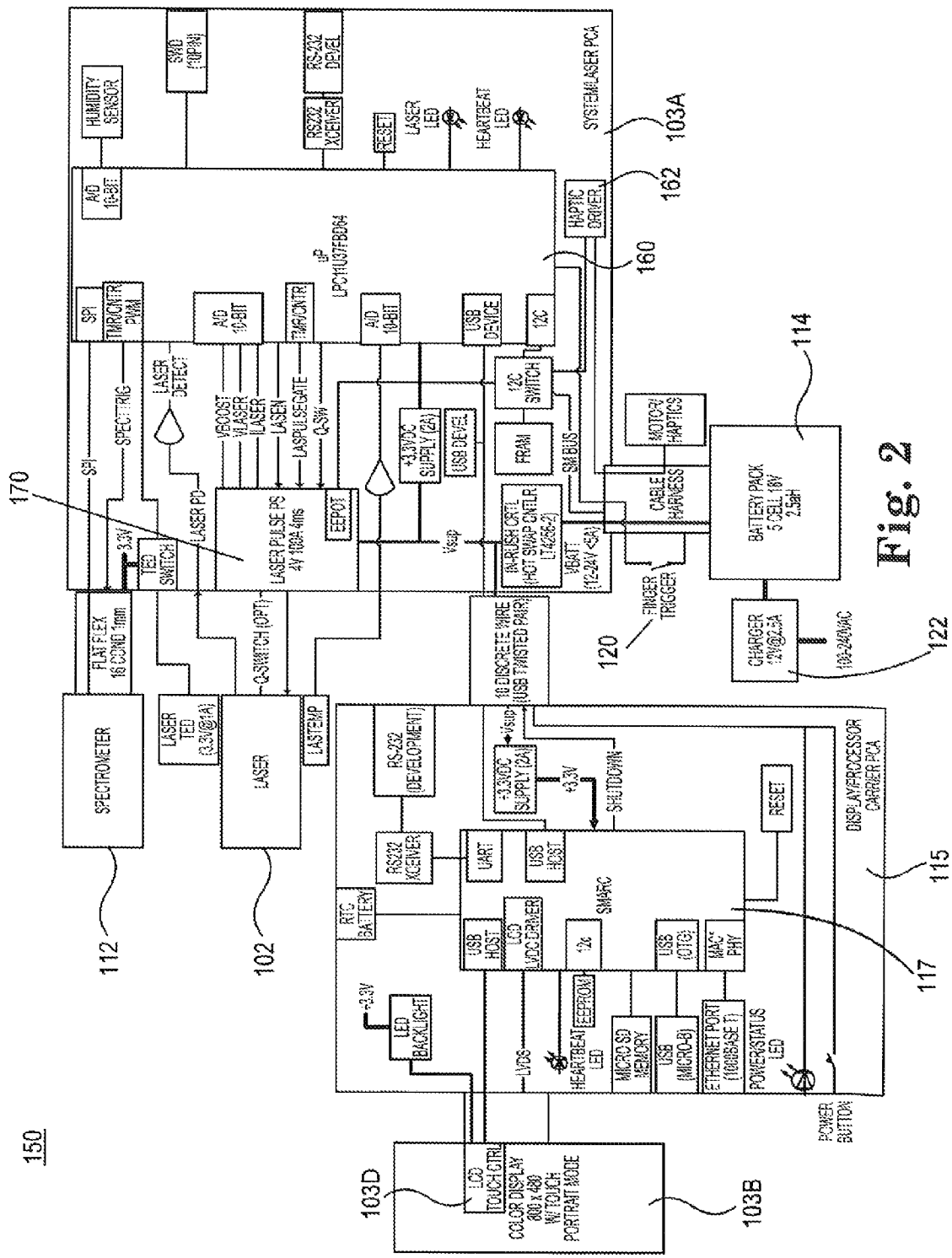
FIG. 2 illustrates a schematic diagram of a LIBS measurement system according to an embodiment of the invention.

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Referring now to FIGS. 1A-1D and FIG. 2, there are various views of a handheld device 100, which has a size and shape for user portability for the purpose of making LIBS measurements. In this example embodiment, handheld LIBS device 100 appears to have a gun-shape and resembles a slightly oversized cordless drill-type housing 101 (see FIGS. 1A and 1B). Inside device 100 is a small 1535 nm passively Q-switched diode pumped solid state laser 102 (with a heat sink thereon 104 located on the top of the device and on external surface of the device) and a controller module 103A and display 103B, controller module 103A being configured to control the operation of the pump laser 102. A laser power supply 107 is operatively coupled to laser 102 while optic holder 106 (1 of a set of 3) operatively couples the laser 102 to laser exit 108. The placement of heat sink 104 allows for faster cooling and allows the user to mechanically use the top part of the heat sink as a sight guide to guide the laser light beam to the region on the sample being targeted.

Device 100 further includes an optical fiber 110 which transmits the laser light emitted by diode pumped laser 102 to a spectrometer module 112. Device 100 features a rechargeable battery, a color touchscreen display 103B (similar to that of smartphone) and a trigger 120 to start the sample analysis process. Optical emissions from a sample (not shown) are collected and conveyed through optical fiber 110 to spectrometer 112, which produces information in electronic form describing the spectral distribution of the optical emissions. This information is transmitted to the controller 103A, which processes and stores the information and can provide visual indications illustrative of said information on display 103B. In addition to the display, the user interface of the apparatus may comprise various switches, of which a trigger switch is schematically shown in FIG. 2. In one example embodiment, handle 116 of device 100 supporting trigger 120 is shielded to provide additional protection to the user from heat and any stray radiation. The operating power needed to operate the apparatus comes from a power source 114, which may be e.g. a battery (regular or rechargeable) or a fuel cell. In a related embodiment, the power source is an AC power source.

Inside this example embodiment, device 100 includes a small 1535 nm passively Q-switched diode pumped solid state laser. There are a series of laser optics to expand and focus the laser beam at the target sample. In this example embodiment, the light from the plasma is collected with a fiber optic and analyzed with a miniature Czerny-Turner spectrometer using a CCD detector. In related embodiments, the light from the plasma is analyzed using other spectrometer and light collection configurations known by those skilled in the art. In this example embodiment, device 100 uses a single board computer inside to control device 100 and process the spectral data. Housing 101 is sealed to NEMA 3 standards and designed for rugged outdoor use. In other related embodiments, eye-safe laser sources ranging from 1500 nm to 1600 nm are also available for portable handheld LIBS systems as described herein.

FIG. 2 illustrates schematically a handheld LIBS measurement system 150 according to an embodiment of the invention. When using handheld device 100, the user makes direct or substantially close contact (about 1 mm) with the test sample with the nose or exit 108 of device 100 to obtain the best results. This is monitored in device 100 with one or more proximity sensors that sense the sample proximity before the laser is fired. At this point a trigger pull will initiate an analysis and the laser will fire a burst of pulses at the sample. The computer (or controller or processor) 103A will process the spectrometer data and provide results to the user in about 3 seconds or less. The LIBS device 100 will generally reveal the alloy type (Aluminum 6061 for example) and the chemical composition (e.g. elemental concentrations). In a related embodiment, system 150 is configurable to provide confidence information on the identification of the alloy type based on the confidence of the spectral information compared to known, allowed constituent concentration ranges.

System 150 includes a Q-switched solid state diode pumped laser module 102 and a spectrometer module 112 that are both electrically coupled to system controller and board 103A. Board 103A includes a microprocessor 160, a haptic driver 162 for feedback of the operation of device 100, and a laser power supply 170 to provide power to laser module 102. Battery pack 14, charger unit 122 and trigger circuit 120 are also electrically coupled to board 130A. System 150 also includes a display processor board 115 that is electrically coupled to board 103A and coupled to display 103B which displays data and serves as a command input device (via LCD touch controller 103D), among other functions. Display board 115 includes a SMARC processor 117 to help manage applications for device 100 at low power and to communicate with the laser control board.

One purpose of firing multiple shots at the sample is to prepare the sample for the analysis and to calibrate the internal components of device 100. A significant number of laser pulses are recommended to remove contamination from the surface of the material to be tested before data is recorded. In one example embodiment, the burst mode is about 10 to about 12 pulses at about 4 kHz. The bursts usually occur at about 10 Hz repetition rate. Generally, every tenth of a second you have a burst of 10-12 pulses with each pulse at a frequency of 4 kHz. The laser energy is about 2-3 mJ (milli-joules) per pulse. The length of time for each pulse is about 6 nanoseconds. In another example, the sample is subjected to pulses at about 4-5 mJ in strength at about a 10 Hz repetition rate.

In the various example embodiments disclosed herein, a Kigre 1535 nm laser source (model MK-88; Kigre Inc., Hilton Head Island, S.C.) is used which is capable of generating a 5 mJ pulse using a 3.5 ms pump pulse. This laser source can provide about 12 pulses with a spacing of about 100 microseconds between each mini or sub pulse in the pulse train. Although Kigre discloses in a related article an eye-safe LIBS system using a 1535 nm laser source (*LIBS system with compact fiber spectrometer, head mounted spectra display and hand held eye-safe erbium glass laser gun*. SPIE Photonics West 2010, Solid State Lasers XIX: Technology and Devices Conference LA101, #7578-87, Jan. 26, 2010), which is herein incorporated by reference in its entirety, the various components for the system are physically carried on the user (such as with a backpack and belt) and are not in a fully integrated single handheld portable unit as taught herein. Although there is discussion in the aforementioned 2010 article on using successive pulses with very short time lapses between pulses (about 25 µs) such pulses typically last 100 µs and are used to interact with and enhance the plasma plume from the previous pulse so as to improve light signal collection from the plume. Finally, the non-integrated system disclosed in the 2010 article above does not address the challenges of thermal management of the laser source when in close proximity with other system components disposed within a single housing of a handheld device.

In various embodiments taught herein, thermal management of the laser source for extending the life of the laser and the battery is achieved by transitioning from the single pulse mode used in the prior art to the pulse train. In the single pulse mode, the temperature of the laser quickly rises or spikes, while in the pulse train mode, the temperature rise is steady and is lower than the single pulse mode, thereby emitting less heat and reducing battery consumption as the laser energy needed to generate the spectral measurements is less. In addition, the multiple data bits generated by the pulses within the pulse train are integrated (in essence added up) by the spectrometer to generate the spectral graph onto the display screen of handheld device 100 for the user to decide how to handle the sample at hand (such as in a sorting application).

Referring now to FIG. 3, there is illustrated a table comparing the measurements from a single pulse mode and a pulse train mode for a particular material sample having known quantities/percentages of Mg, Cu and Al. As the chart is reviewed from left to right, the single pulse mode generates first an identification and accuracy of the presence of the element. The more samples are taken the more precise the measurement, hence the number value in the column decreases to show that the measurement and technique exhibits a more accurate identification of the presence of that one element. At 150 shots of the single pulse shots, all of the values are low indicating a higher degree of accuracy.

The pulse train mode on the other hand (right side of table) illustrates that one shot of a pulse train provides a more accurate reading than one shot of a single pulse. Further, 15 shots (with each having 10 pulses) of the pulse train mode, which is equivalent to 150 total pulses, generates a spectral reading that is both more accurate than the 150 individual pulses in the single pulse mode and acquired in substantially less time.

Referring now to FIGS. 4-9, FIGS. 4A-4C, 5 and 9 illustrate a side, back and front view as well as an internal view of another LIBS measurement apparatus 400 according to another embodiment of the invention. This example embodiment of a handheld LIBS measurement apparatus has various advantages including: an active Q-switched laser module that facilitates immediate laser firing upon depressing a trigger on the handheld unit, a sampling cone interface member for enhancing laser focusing and to assist with the capture of light signals from the sampled material (to and from the handheld LIBS device), and at least two compact spectrometers that provide spectral distributions over a wide range of wavelengths to not only pick up weak light signals but also to be able to identify a wide range of materials with a wide range of spectral signatures. Also, higher resolving power with multiple spectrometers, allows for materials with many emission peaks to be discriminated, like iron alloys. An advantage to the spectrometers taught herein is that the spectrometers operate with specialized transmission gratings to provide well defined spectral distributions that are displayable real time to the user on a display on the handheld device. Use of transmission gratings provide more light throughput (hence improved efficiency and sensitivity) than similarly sized reflection gratings that are used by other spectrometers in the art. This is important in applications where the energy of the signal emitted from the sampled material is low due to lower power/energy beams being projected by the LIBS device and where the little light or sample emitted energy that is left that has to be processed efficiently and effectively. Further examples and teachings on spectrometers with transmission gratings are found in U.S. Pat. No. 7,515,262, which is incorporated by reference in its entirety In one example embodiment of the laser module, an Nd:YAG laser contains an OPO (Optical Parametric Resonator) that converts the 1064 nm Nd:YAG wavelength to 1574 nm. In operation when the trigger is pulled the laser is triggered at a 20 Hz (50 ms) rate. A spectrum is collected for each shot. Some shots are discarded (cleaning) but each can be used independently for analysis or averaging. The sample ends when sufficient data is collected for confidence in the measurement, or when an error is detected such as when the user is not holding the sample material to the sampling cone interface correctly, or when a predetermined number of shots have fired, (100 shots-5 seconds). In a related embodiment, there is a built-in ability to delay the spectrometer module timing aperture (0 to 10 us) to start the collection slightly after the initial LIBS plasma is formed. We are not using this feature now (delay always=0), but the hardware will allow us to explore this common LIBS technique and allow for better dynamic range with our CCD-based spectrometer detectors and improve sensitivity in the measurement of certain elements. This is a dynamic setting that can be applied on a shot by shot basis as well as having independent delays for each spectrometer. This delay feature cannot be exploited with the passive Q-switch laser systems since it requires precision timing (approx. <20 ns) between the laser pulse and the spectrometer shutter.

Further, with an active Q-switched laser, there is provided a tunable/controllable laser with very high shot to shot laser energy precision as well as a spectrometer with controllable sensitivity at the detector such that calibration from device to device is more easily attained. This also facilitates remote calibration without the need to return the unit to the factory for calibration as libraries can be added or sold in the field. The active Q-switched approach provides high shot to shot reproducibility so as to obtain very fast analyses. The fast analysis allows for "contact-based" triggering and analysis, similar to a contact based triggering found in a nail gun. Deeper analysis is also possible with this embodiment and laser mode thereby avoiding the need for rastering optics or having to raster the sample. The deeper penetration allows for a larger spot size and deeper analysis as well as an improved depth of focus, thereby facilitating the use of a point in sampling of the material. Having a sharp sampling point provides for easier sample to instrument interfacing and for sampling non-flat surfaces. In a related embodiment, two operating modes are possible to allow for cleaning and sample analysis. Laser energy can be at a first energy level of 10 mJ at 10 Hz or a second energy level of 5 mJ at 20 Hz, with the first energy level for cleaning (higher power) and the second energy level for analytical acquisition. These power levels can be controlled with a power control trigger In this example embodiment, handheld LIBS device 400 includes a housing 401 that resembles a slightly oversized cordless drill. Housing 401 has therein a small 1574 nm actively Q-switched diode pumped solid state laser module 402 supported by an optic holder 406. Referring again to FIGS. 5 and 9A-9B, a heat sink 404 for laser module cooling is provided and is located on the top and external surface of the device, while a display 403 is located on housing 401. Device 400 also includes a controller module 405 configured to control the operation of pump laser module 402. A laser power supply 407 is operatively coupled to laser 402 while an optic holder 406 operatively couples laser module 402 to a sampling cone interface 408 at laser exit 409. At an exit of cone interface 408 is also located (adjacent to the laser beam from laser module 402) an optical fiber that picks up the light signal from the sampled material. The location of heat sink 404 allows for faster cooling of device 400 and allows the user to mechanically use the top part of heat sink 404 as a sight guide to guide the laser light beam to the region on the sample being targeted.

In one example embodiment, the active Q-switched laser is configured to provide 5 samples per minute, with about 60 pulses per sample and 12 seconds between samples. In a related embodiment, less than 3 seconds is provided between samples. In another example embodiment, the first five shots are shuttered to allow for thermal stabilization (resonator thermal stabilization). The laser module operates at 24 volts DC, with current levels as follows: stop mode <70 mA; fire mode 1.2 A and power mode of <30 W.

Figure 4:
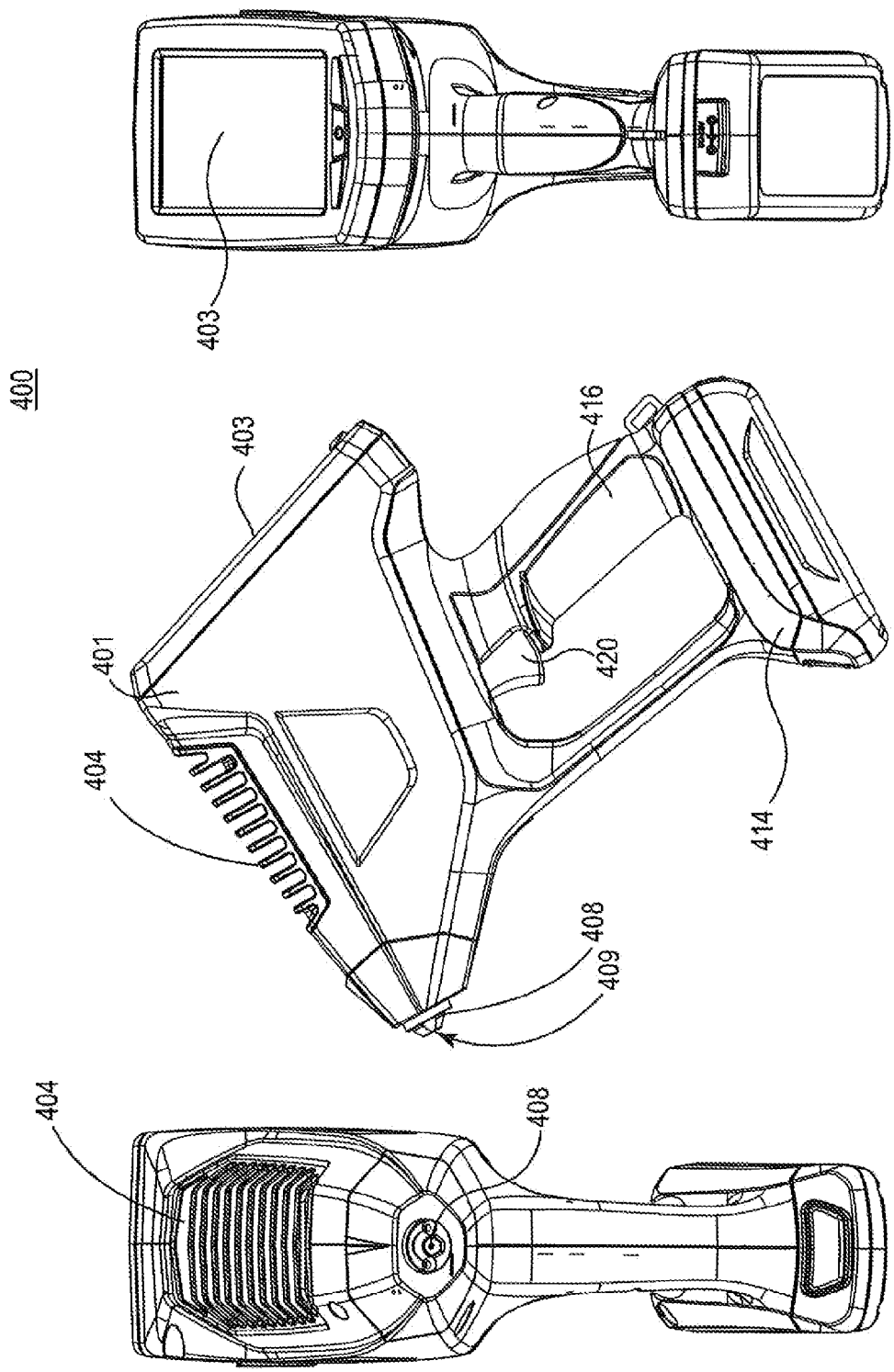
FIGS. 4A-4C illustrate a side, back and front views of a LIBS measurement apparatus according to another embodiment of the invention.
Figure 5:
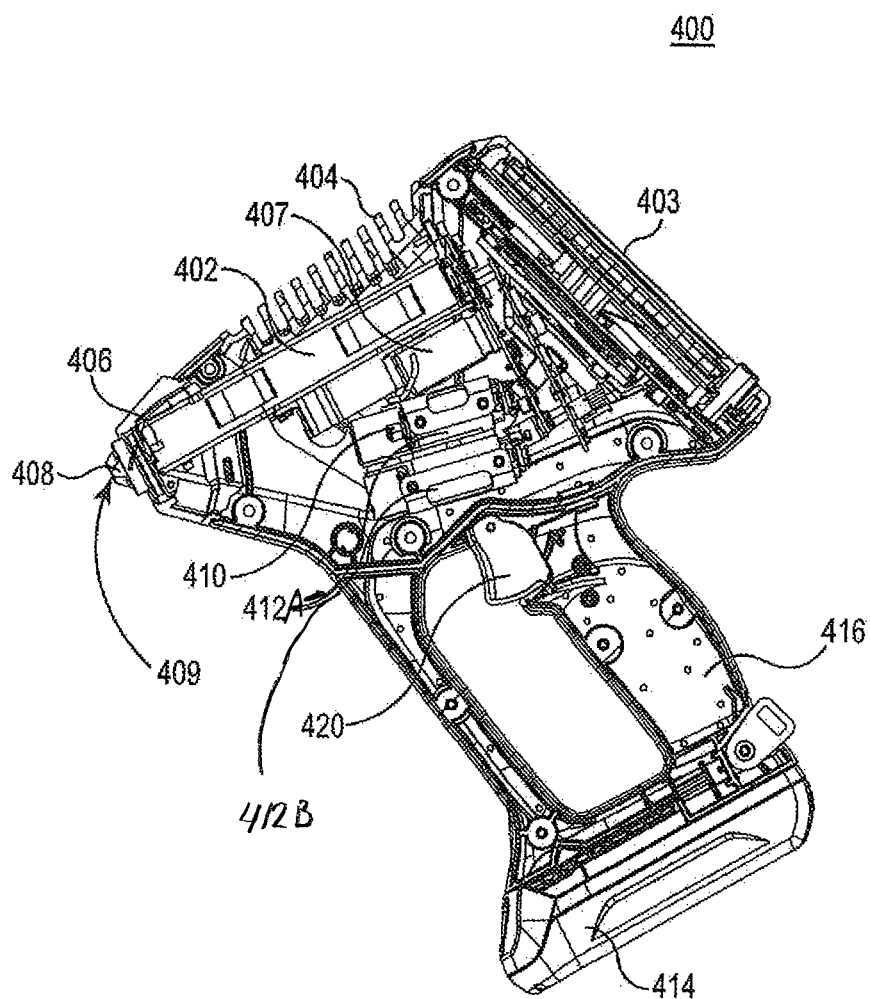
FIG. 5 illustrates an internal view of the components of the LIBS apparatus of FIG. 4.

FIGS. 5 and 9A and 9B illustrate an internal view of the components of the LIBS apparatus of FIG. 4. Device 400 further includes an optical fiber 410 which conducts or transmits the laser light emitted by the sampled material, after pump laser 402 is fired, to a set of spectrometers 412A and 412B (comprising a spectrometer module). Device 400 features a rechargeable battery 414, a color touchscreen display 403 (similar to that of smartphone) and a trigger 420 to start the sample analysis process. Optical emissions from a sample (not shown) are collected and conveyed through optical fiber 410 to spectrometers 412A and 412B, which produce information in electronic form describing the spectral distribution of the optical emissions originating from the sample. This information is transmitted to a controller 405, which processes and stores the information and can provide visual indications illustrative of the information on display 403. In addition to the display, the user interface of the apparatus may comprise various switches, of which a trigger switch 420 is shown in FIGS. 4A and 5. In one example embodiment, the handle of device supporting trigger 420 is shielded to provide additional protection to the user from heat and any stray radiation The operating power needed to operate the apparatus comes from a power source 414, which may be a battery (regular or rechargeable) or a fuel cell. In a related embodiment, the power source is an AC power source.

Inside this example embodiment, shown in FIGS. 5 and 9A and 9B, device 400 includes a series of laser optics to expand and focus the laser beam at the target sample. The light from the plasma generated by the laser shot is collected with a fiber optic member 410 in a holder 406 and analyzed with spectrometers 412A and 412B. The device uses a PCB board computer inside to control the unit and process the data. The housing is sealed to NEMA 3 standards and designed for rugged outdoor use. In other related embodiments, eye-safe laser sources ranging from 1500 nm to 1600 nm are also available for incorporation into the various embodiments of portable handheld LIBS systems described herein.

Figure 6:
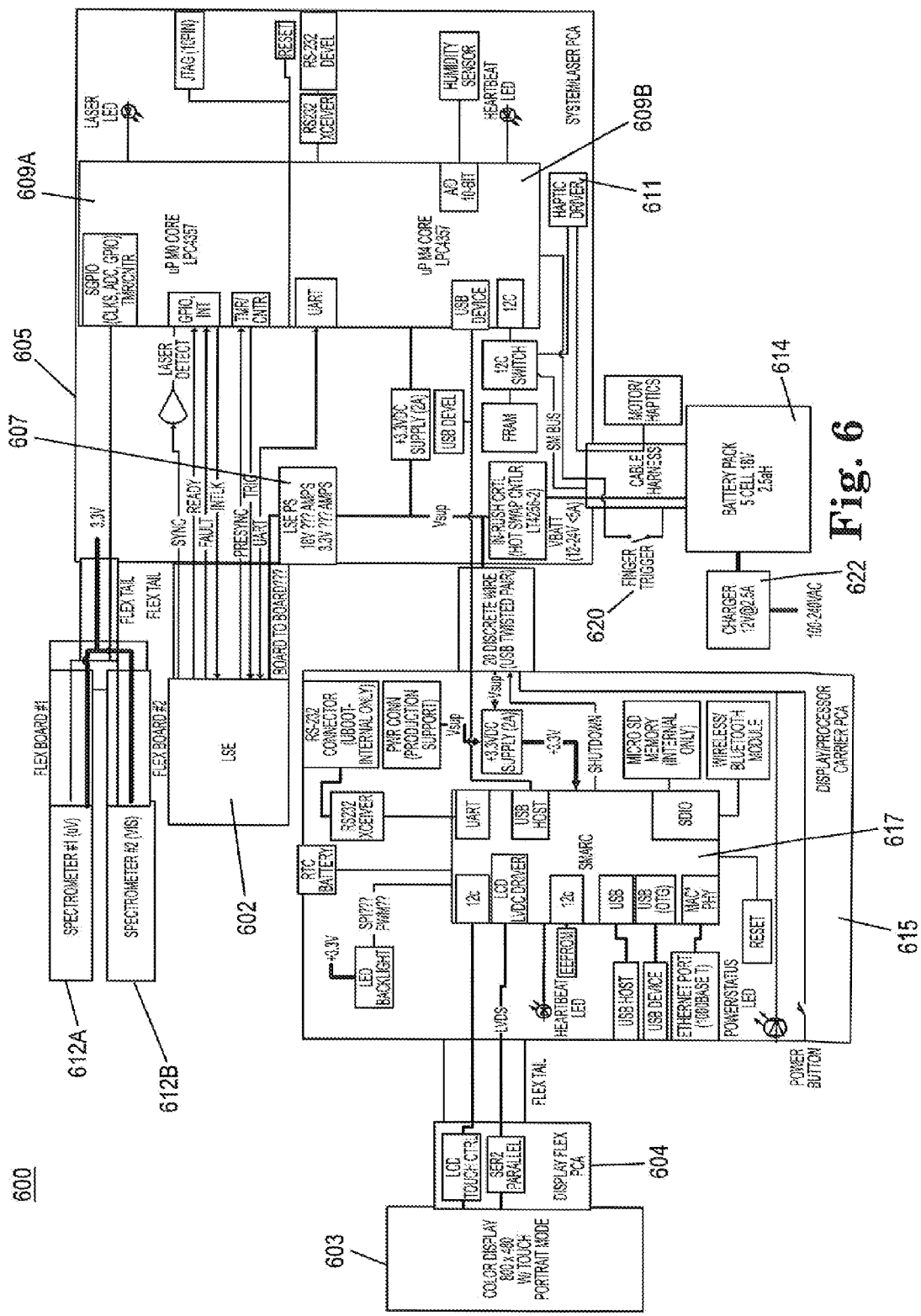
FIG. 6 illustrates a schematic diagram of the LIBS measurement apparatus of FIG. 4.

FIG. 6 illustrates a schematic diagram 600 of an example embodiment of LIBS measurement apparatus 400 of FIG. 4. When using handheld device 400, the user makes direct or substantially close contact (about 0.5 cm) with the test sample with sampling cone interface 408 of device 400 to obtain the best results. Sampling cone interface 408 allows the user to use a smaller surface size to obtain a sample signal from the sample material as well as provides the user with a deeper penetration at that spot, thereby overcoming challenges with non-smooth surfaces on sample materials. In one example embodiment, device 400 is monitored with one or more proximity sensors that sense the sample proximity before the laser is fired. At this point a trigger pull will initiate an analysis and the laser will fire a plurality of laser shots at the sample. The computer (or controller or processor) processes the spectrometer data and provides results to the user in about 3 seconds or less. The LIBS device will generally reveal the alloy type (Aluminum 6061 for example) and the chemical composition (e.g. elemental concentrations) if desired.

In this example embodiment, with an active Q-switched optical parametric oscillator Nd:YAG laser module firing multiple shots at the sample to prepare the sample for the analysis and to calibrate the internal components of device 400 is not necessary (but it is an option if sample cleaning is desired) as the laser module is configured for instantaneous laser emission upon actuating the trigger. In this example embodiment, the laser operates at a wavelength of 1547 nm, at an energy level of 5 mJ (milli joules) at a repetition rate of about 20 Hz. The device has a numerical aperture of >0.0555. The length of time for each pulse is about 6 nanoseconds. In another example, the sample is subjected to pulses at about 4-10 mJ in strength at about a 20 Hz repetition rate. Further examples and teachings on Nd:YAG OPO laser modules and operating parameters and burst pulses are found in U.S. Pat. No. 7,839,904, which is incorporated by reference in its entirety. The laser module specifically includes a gain block, such as a Nd:YAG gain block, a Q switch, and an optical parametric oscillator (OPO) crystal (e.g., a KTP nonlinear frequency-conversion crystal) on a substrate 10 (e.g., an undoped YAG rail). A highly reflective (HR) mirror may be disposed at one end of the gain block, an output coupler (OC) mirror may be disposed at an end of OPO crystal, and a dichroic mirror may be disposed between the HR mirror and the OC mirror (e.g., between the Q switch and the OPO crystal). In one example implementation, the OC mirror (e.g., 60% R 1574/HR 1064 deposited on the end of the OPO crystal) may pass a portion of light at a wavelength of 1574 nm as a final output of the laser module, while reflecting light at a wavelength of 1064 nm back into the OPO crystal (e.g., a KTP crystal). The dichroic mirror (e.g., HR 1574/AR 1064 deposited on the OPO crystal or the Q switch) allows through light at a wavelength of 1064 nm, while reflecting light at a wavelength of 1574 nm back into the OPO crystal. The HR mirror (e.g., HR 1064 deposited on the end of the gain block) reflects light at a wavelength of 1064 nm back into the gain block, which generates light at a wavelength of 1064 nm when provided with an appropriate optical pumping light source, as would be understood by one skilled in the art. The laser module is configured in this exemplary embodiment in an internal OPO configuration (intracavity OPO sub-resonator), with a first resonant cavity formed between the mirror and the OC mirror and a second resonant cavity formed within the first resonant cavity between the dichroic mirror and the OC mirror.

Referring again to FIG. 6, system 600, in this example embodiment, includes laser module 602, which is an active Q-switched, optical parametric oscillator Nd:YAG laser operating at a wavelength of 1574 nanometers, that is electrically coupled to a laser power supply 607 and coupled to a pair of microprocessors 609A and 609B that are on a controller circuit assembly or board 605. Board also includes a haptic driver 611, which is electrically coupled to a haptic motor assembly, and is coupled to trigger circuit 620, battery pack 614 and to charger circuit 622. After laser module 602 fires, at least one of a pair of spectrometers 612A and 612B receives from a fiber optic member (or other energy or radiation transmission member or medium) the light signal from the sample and generates a spectral distribution that is displayed on display 603. In this example embodiment, spectrometer 612A is configured for light signals predominately in the ultraviolet (UV) range while spectrometer 612B is configured predominately for visible light. Display 603 is electrically coupled to a display flex board 604 which in turn is electrically coupled to a display processor assembly 615 that provides a SMARC processor 617 for controlling display 603 and other external inputs to the handheld LIBS unit such as wireless modules for communicating data to and from the unit, a memory module for data storage, a power button, an Ethernet (RJ45) input connector and a USB connection input. In this example embodiment, processor assembly 615 is electrically connected to controller assembly 605 to receive power as well as data from the spectrometers that are to be displayed to the user. In this example embodiment, a battery pack unit 620 with a charger unit 622 is electrically coupled to board 605.

Figure 7:
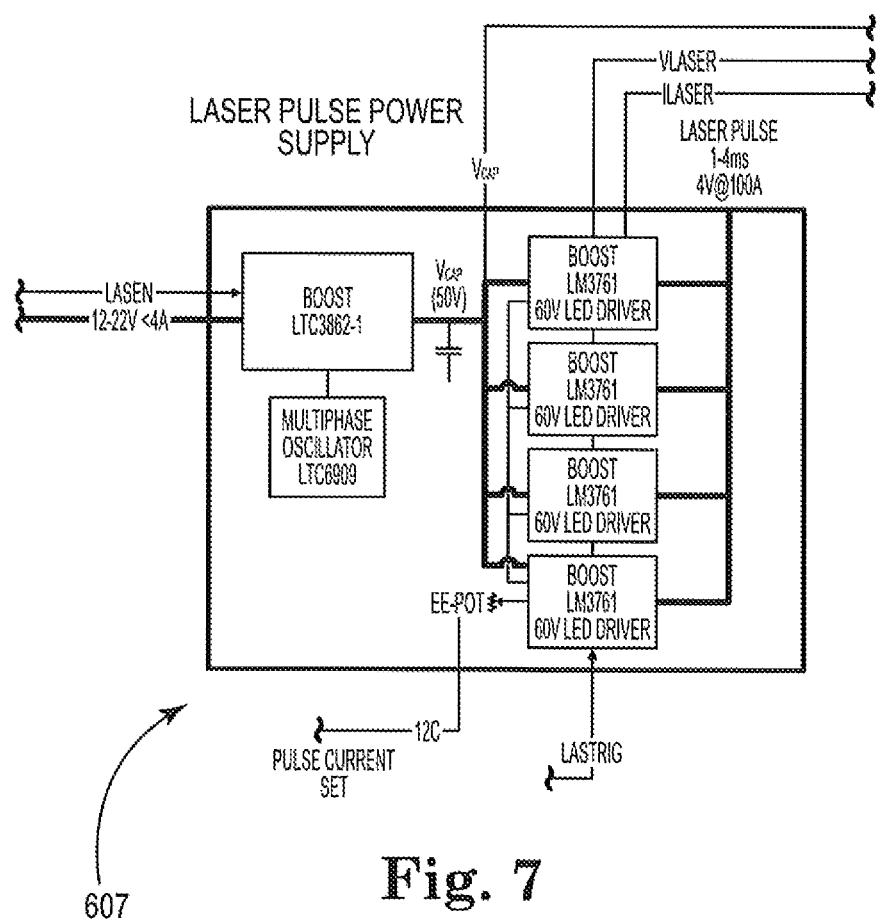
FIG. 7 illustrates a schematic of a laser pulse power supply of the invention.
Figure 8:
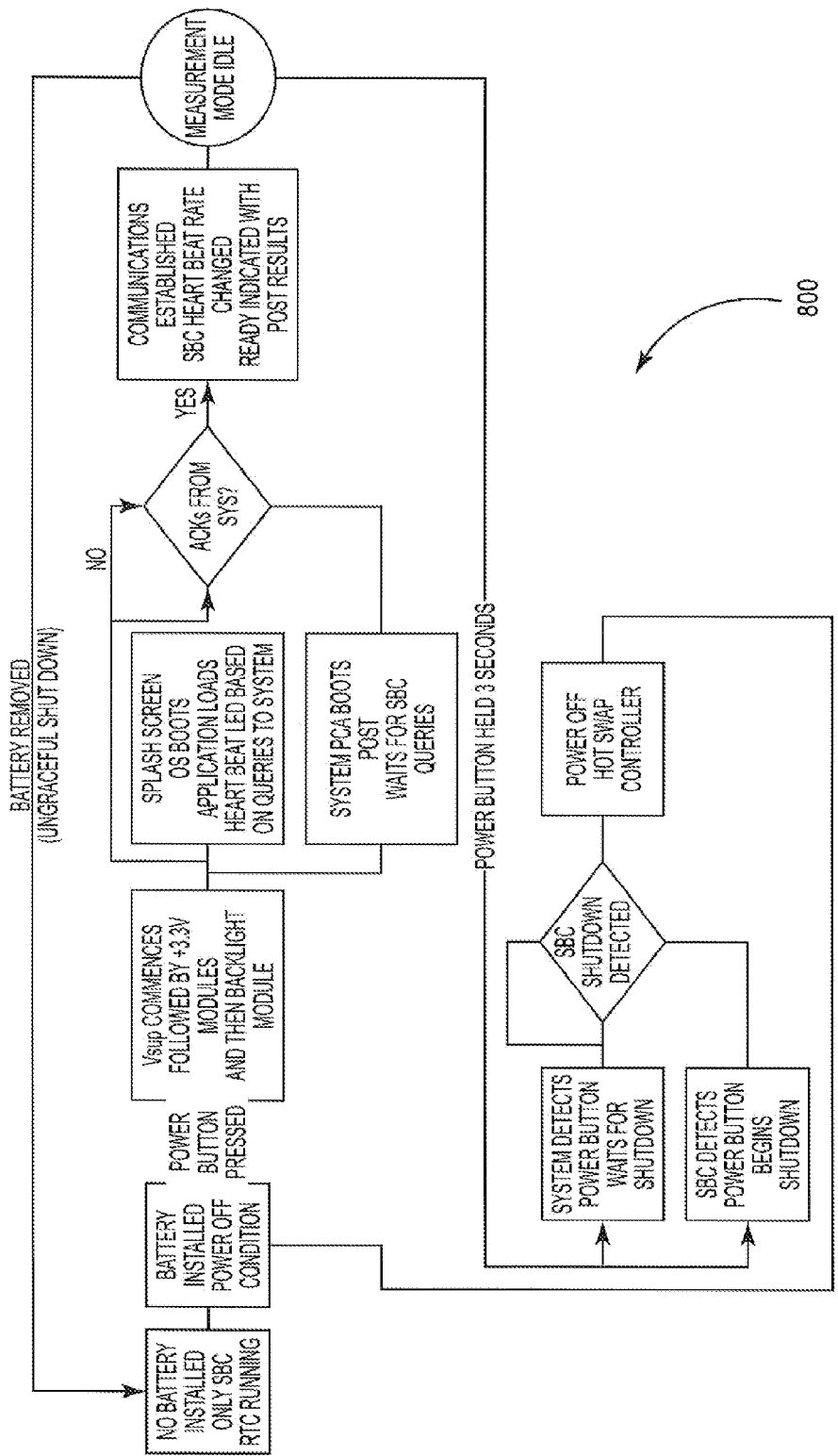
FIG. 8 illustrates a flowchart of a shutdown scheme of the LIBS apparatus of FIG. 4 when a battery or power source is removed from the apparatus.

Referring now to FIG. 7 illustrates a schematic of an example laser pulse power supply 607 for handheld LIBS devices 100 and 400. FIG. 8 illustrates a flowchart of an example shutdown scheme of LIBS devices 100 and 400 when a battery or power source is removed from the handheld LIBS apparatus.

Referring now to FIGS. 9A and 9B, they illustrate side and enlarged views of a sampling interface member in the form of a cone 408 according to the teachings of the invention. The sampling interface member (cone or cylinder shaped, but not limited to same) is an advancement in the art in that there does not appear to be a viable handheld XRF or handheld LIBS solution in the market with a sharp tip or radiation focused feature on it. Most current analyzers have flat, long sampling interfaces. Consequently, this embodiment does not need a camera for image capturing, nor does it need auto-focusing, nor a need to grind down the sampling surface for flatness. Instead, the embodiments described herein provide a laser beam or radiation stream similar to a drill bit (small in diameter, and easy to see as it protrudes away from the housing). In a related embodiment, a longer interface and a smaller point size, through the use of a pierced mirror to transmit or transfer light, for instance but not necessarily limited to same, instead of a fiber, to a spectrometer can minimize the sample-to-instrument distance dependence and reduce the likelihood of a laser window from getting dirty (i.e. lower maintenance). In addition, the sampling interface member can ensure that the plasma does not interact with the cone, or cause cross-contamination with the window or lens.

9A there is shown a side view of device 400 with a sampling interface member 408 and laser exit 409. Also shown is laser power source 407 and laser control board 405. In an enlarged view of the exit portion of device 400, there is shown laser 402 emitting a laser beam through exit 409 through sampling interface member 408. Adjacent to the laser beam and exit 409 and within cone 408 is an optic fiber 410 with a ferrule 410A such that a distal end of fiber 410 captures and transmits light energy emitted from a sampled material and transfers same to a spectrometer module for processing. In a related embodiment, the interface member 45 is in the shape of a cylinder.

In a related embodiment, an apparatus for performing laser-induced breakdown spectroscopy (LIBS) is provided that includes a housing configured as a handheld apparatus having an exit for electromagnetic radiation generated from within the housing and an electromagnetic radiation module with a controller system operatively coupled thereto disposed within the housing, the electromagnetic radiation module configured to direct electromagnetic radiation through the exit. The LIBS apparatus also includes an electromagnetic radiation transfer member configured to transfer or transmit emitted radiation from a sample material after reacting with the electromagnetic radiation. Also included is a spectrometer module configured to receive the transferred radiation and configured to produce a spectral distribution corresponding to the sample material and a sampling point interface member with a proximal opening disposed over the housing exit, the electromagnetic radiation adapted to be projected through the proximal opening and through a distal opening of the interface member, the transmit member being disposed adjacent the interface member distal opening, wherein the sampling point interface member eliminates autofocusing and increases electromagnetic radiation transfer or transmission by the transfer member.

Primary applications for handheld device 100 include but are not limited to: 1) the scrap aluminum area where users need something faster and easier to use than the market leading XRF guns, and 2) secondary aluminum smelters which accept aluminum scrap, to value and verify the scrap as it comes in. Other applications include analysis of other non-ferrous metals, ferrous metals and soils.

The following patents that relate to such LIBS devices are herein incorporated by reference in their entirety and constitute part of the disclosure herein: U.S. Pat. Nos. 7,394,537; 7,821,634 and U.S. Pat. Publ. No. 2012/0033212.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

What is claimed is:

1. An apparatus for performing laser-induced breakdown spectroscopy, comprising:
  a housing configured as a handheld apparatus having an exit for electromagnetic radiation generated from within the housing;
  an intracavity, active Q-switched OPO Nd:YAG diode pumped solid state laser module that operates at an eye-safe wavelength of about 1574 nanometers and provides instantaneous laser emissions upon actuation, with a controller system operatively coupled thereto disposed and within the housing, the intracavity laser module including a reflective mirror and an output coupler mirror that form a first resonant cavity and form a second resonant cavity within the first resonant cavity for directing a laser beam through the exit with an energy level per pulse from about 4 millijoules (mJ) to about 10 millijoules (mJ), wherein the laser module operates at a power mode of about 30 watts or less, and wherein the active Q-switched Nd:YAG OPO diode pumped solid state laser module and the laser beam operate with a numerical aperture as low as about 0.0555;
  a fiber optic member disposed substantially in the housing for transferring light collected at a distal end of the fiber member without a collection lens or reflective mirror from a plasma induced of a sample material by the laser beam, the fiber optic member distal end being disposed adjacent the exit;
  a spectrometer module disposed substantially in the housing for receiving light from a proximal end of the fiber optic member, the spectrometer module producing a spectral distribution corresponding to the sample material from the received light, wherein the controller system provides timing and control between the laser pulse and a spectrometer shutter of the spectrometer module; and a sampling point interface member with a proximal opening disposed over the housing exit, the laser beam adapted to be projected through the proximal opening and through a distal opening of the interface member, the fiber optic member being disposed adjacent to the interface member distal opening, wherein the sampling point interface is configured in the shape of a cone member, the cone member having an opening opposite an exit opening disposed over the housing exit, wherein an end of the cone member includes a housing-to-sample material interaction section disposed about the housing exit, the interaction section having an area of less than about 2 cm^2.

2. The apparatus according to claim 1, wherein the spectrometer module includes a first spectrometer configured to operate in an ultraviolet wavelength range and a second spectrometer configured to operate in a visible wavelength range.

3. The apparatus according to claim 2, wherein the first and second spectrometer include a transmission grating.

4. The apparatus according to claim 1, further comprising a power source disposed within said housing and configured to deliver electric power to at least said laser module and said spectrometer module.

5. The apparatus according to claim 1, further comprising a display configured to display information and to receive commands from a user.

6. The apparatus according to claim 1, further comprising a sighting member configured to assist a user in directing the laser beam, wherein the sighting member is selected from the group consisting of a heat sink member disposed above the laser module and a targeting LED member adapted to project light at a target on the sampled material.

7. The apparatus according to claim 1, further comprising at least one proximity sensor near the housing exit, the proximity sensor configured to sense location of sampled material.

8. The apparatus according to claim 1, further comprising a haptic feedback module for providing feedback that a sample analysis is at an acceptable precision level.

9. The apparatus according to claim 1, wherein the spectrometer module includes a timing aperture or shutter configurable to delay for a predetermined time the collection of light after an initial plasma is formed.

10. The apparatus according to claim 1, wherein the OPO diode pumped laser module provides about 5 samples per minute, with about 60 pulses to about 100 pulses per sample, and less than about 3 seconds to about 12 seconds between samples.

* * * * *